United States Patent [19]

Ström et al.

[11] Patent Number: 5,410,907

[45] Date of Patent: May 2, 1995

[54] GAS SAMPLING METHOD AND DILUTION TUNNEL THEREFOR

[76] Inventors: Hans Ström, Bräcke 14003, 44260 Kode; Roy Ekdahl, Tranbärsvägen 65, 44800 Floda, both of Sweden; Edwin S. Harbuck, 104 Carrollton Ave., Shreveport, La. 71105

[21] Appl. No.: 111,843

[22] Filed: Aug. 25, 1993

[51] Int. Cl.⁶ ............................................. G01N 1/22
[52] U.S. Cl. ................................. 73/23.31; 73/31.07
[58] Field of Search .................... 73/23.31, 23.32, 116, 73/117.3, 863.03, 863.81, 864.43, 31.07

[56] References Cited

U.S. PATENT DOCUMENTS

| | | | |
|---|---|---|---|
| 3,603,155 | 9/1971 | Morsis | 73/23.31 |
| 3,699,814 | 10/1972 | Kaufman . | |
| 3,817,100 | 6/1974 | Anderson et al. . | |
| 3,892,549 | 7/1975 | Lyshkow . | |
| 3,917,454 | 11/1975 | Clark | 73/23.31 |
| 3,965,749 | 6/1976 | Hadden et al. . | |
| 3,986,386 | 10/1976 | Beltzer et al. . | |
| 4,586,367 | 5/1986 | Lewis . | |
| 4,633,706 | 1/1987 | Ito et al. . | |
| 4,654,058 | 3/1987 | Schober et al. . | |
| 4,660,408 | 4/1987 | Lewis . | |
| 4,747,297 | 5/1988 | Okayama et al. . | |
| 4,974,455 | 12/1990 | McGowan et al. . | |
| 5,058,440 | 10/1991 | Graze, Jr. . | |
| 5,090,258 | 2/1992 | Yamasaki et al. . | |
| 5,184,501 | 2/1993 | Lewis et al. . | |

*Primary Examiner*—Richard E. Chilcot, Jr.
*Assistant Examiner*—Patel Harshad

[57] ABSTRACT

Emission gasses from an engine exhaust pipe are collected through an inlet of a dilution tunnel which is an elongated, hollow tube. The inlet is spaced from the exhaust pipe to also admit surrounding air. The air and emissions are mixed in the tunnel by a screen in the tunnel. A probe in the tunnel diverts a portion of the mixture to gas analyzers. Prior to analysis the mixture may be condensed, filtered or otherwise processed.

20 Claims, 2 Drawing Sheets

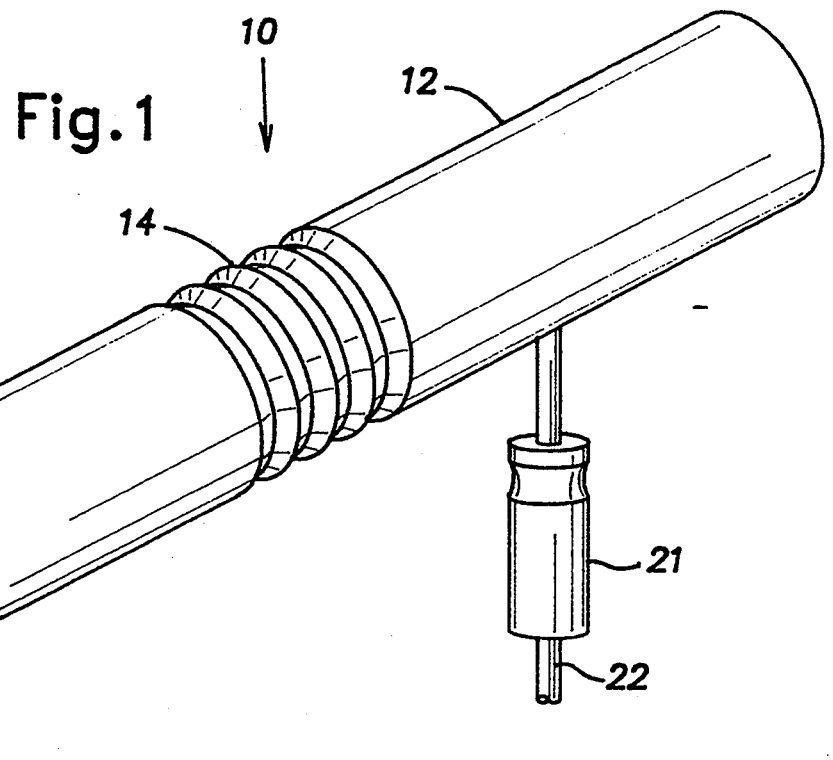
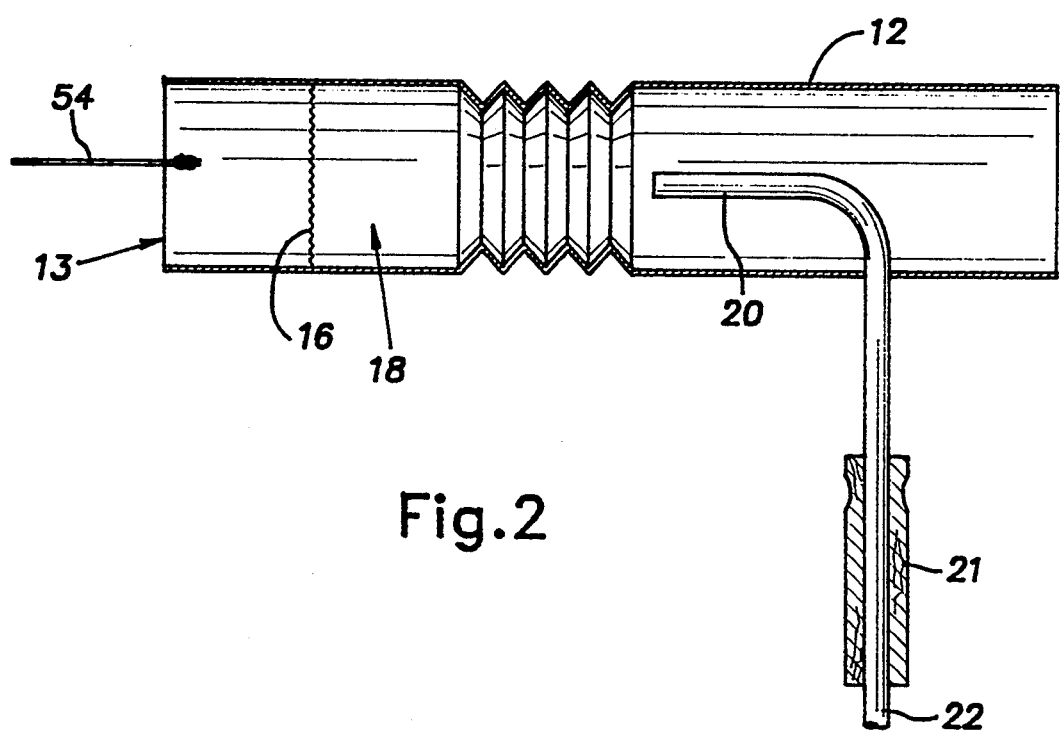

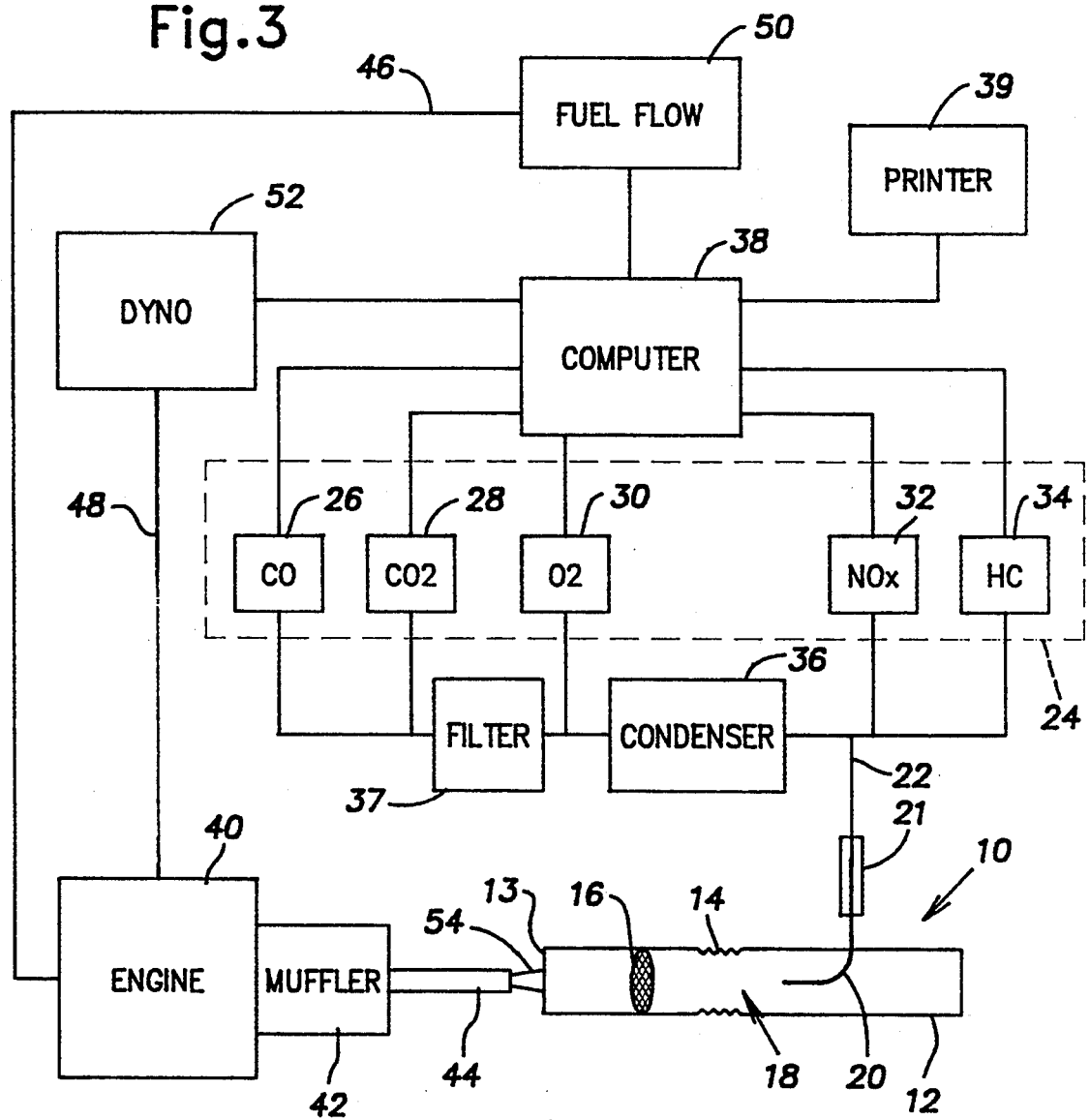
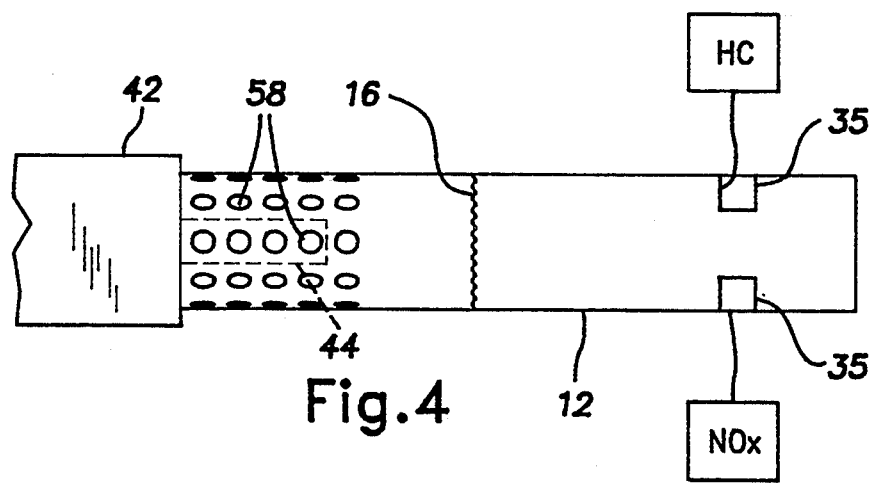

GAS SAMPLING METHOD AND DILUTION TUNNEL THEREFOR

BACKGROUND OF THE INVENTION

1. Field of the Invention

This invention relates generally to the field of analysis of emission gasses and specifically to an improved dilution tunnel for collecting the gasses.

2. Description of the Related Art

Exhaust emissions from internal combustion engines in automobiles and other vehicles are strictly regulated by the United States Government and other authorities. Emissions from vehicles and machines using smaller engines, such as chain saws lawn mowers, and blowers are also a matter of concern. Thus, numerous regulations and standards have been promulgated setting forth acceptable levels of emissions from such engines. Engines also must comply with regulations regarding air/fuel ratios. To measure emissions and determine compliance with the regulations, it is necessary to test the emissions and performance of such engines.

Numerous gas analyzers are known and available for determining the nature and quantities of the various components comprising the exhaust gas, including carbon monoxide, carbon dioxide, and hydrocarbons. Results are calculated based on measured levels in accordance with SAE J1088 and other standards.

To achieve accurate results it is necessary to properly collect the gas to be analyzed. In many cases, collection and testing are performed during final assembly of the machines or vehicles. Many engines are tested in succession by unskilled workers. Thus, gas collecting and testing apparatus should be simple to operate and easy to move from one engine to the next. One known collection method uses a probe inserted into a muffler of the exhaust system of an engine to be tested. The probe directs a sample of the exhaust to the analyzing apparatus. This method is relatively simple, but is highly dependent on the location of the probe. Different results are achieved at different locations and inaccurate results are obtained if the probe is not properly located. Typical causes of inaccuracies are incomplete mixing of the gasses in the muffler and introduction of atmospheric air into the sample. Inserting probes into the mufflers of engines on an assembly line is burdensome and prone to inconsistencies.

More consistent and accurate results have been achieved with an apparatus known as a mixing chamber, as described in SAE J1088. This is a heated metal box fastened to the outlet pipe of the muffler. The components of the exhaust gas are completely mixed in the chamber before being admitted to the sample probe and directed to the analyzing apparatus. The volume of the mixing chamber is at least 10 times, and usually 100 to 200 times, the cylinder displacement of the engine being tested. However, the size must be selected so that the temperature inside can be maintained at a level which will prevent hydrocarbons from condensing. The outlet of the chamber must be constructed so as not to have a tuning effect on the engine. The design of the chamber and the fastening means may affect engine performance, thus, mixing chambers are uniquely designed for each type of engine tested. Whereas mixing chambers are accurate, they are bulky, complex, and require substantial set-up time. Attaching the mixing chamber to engines on an assembly line is burdensome and time consuming. Maintaining adequate chamber temperature is an additional problem.

A dilution tunnel is another device used to collect the exhaust gasses for analysis. The dilution tunnel has one inlet which is fastened to the exhaust outlet pipe. A second inlet is connected to a source of dilution air or other gas which is to be mixed with the exhaust gas prior to analysis. It is well known in the art that it is desirable to dilute the exhaust gas with atmospheric air in a carefully controlled proportion. Dilution tunnels of this type are shown in U.S. Pat. Nos. 3,699,814; 3,817,100; 3,892,549; 3,965,749; 3,986,386; 4,586,367; 4,633,706; 4,654,058; 4,660,408; 4,747,297; 4,974,455; 5,058,440; 5,090,258; and 5,184,501. As with mixing chambers, the disadvantages of dilution tunnels according to the prior art are bulk, complexity, and long setup time. Also, it is necessary to fasten the tunnel to the exhaust outlet and a source of dilution air, which is troublesome in an assembly line where many engines are tested in succession.

Accordingly, it is desirable to have a device for collecting and analyzing exhaust gasses which is small, lightweight, and easily set up. Such a device should be adaptable for testing large numbers of engines in succession and should be simple and inexpensive to operate, while providing consistent and accurate results.

SUMMARY OF THE INVENTION

The present invention provides a device for testing gaseous emissions from a source. A dilution tunnel has an elongated, hollow tube. An inlet of the tube is adapted to be spaced from the source so as to admit emissions and surrounding air into the dilution tunnel through the inlet. Means are provided for analyzing the emissions in the tunnel.

The device is provided with a means for spacing the inlet from the source, such as a bracket, support, or handle. Since the tunnel is not fastened to the source, it can be supported by a robot or stationary support adjacent an assembly line carrying emissions generating engines. Thus, no operator is required to set up the tunnel. A probe located in the tunnel, such as a hollow tube opening toward the inlet, diverts emissions and air to analyzers outside the tunnel. Alternatively, sensors connected to the analyzing means are located in the tunnel. A means for facilitating mixing of the air and emissions, such as a screen, mesh or steel wool, is disposed in the tunnel downstream of the inlet.

A means for treating the emissions and air, such as a condenser, filter, water trap, or pump, is disposed between the probe and at least part of the analyzer.

A computer is connected to the analyzers to process data and control the analyzers. A fuel flow meter is connected to the computer and a fuel line, and a dynamometer is connected to the computer and a drive shaft. These are used to monitor engine performance with respect to emissions.

A method of testing gaseous emissions from a source is also disclosed. An inlet of a dilution tunnel comprising an elongated, hollow tube is located a selected distance from the source so as to be spaced from the source so as to admit emissions and surrounding air into the tunnel through the inlet. Then, the emissions in the tunnel are analyzed.

In addition, the air and emissions in the tunnel are mixed. A portion of the emissions and air in the tunnel are diverted by a probe means disposed in the tunnel to a means for analyzing the emissions wherein the emissions diverted by the probe are the emissions analyzed.

Tests according to the invention have compared favorably with tests using a mixing chamber, while providing the advantages described herein. Gas samples diluted by surrounding air require less maintenance and cleaning of the analyzer and less frequent filter replacement. Dilution lowers the dew point of the emissions to prevent condensation of hydrocarbons. Placement of the dilution tunnel and the degree of dilution are not critical for accurate measurements. One dilution tunnel can be used for many different types of engines without modification. Because there is no connection to the emissions source, there is no effect on engine performance.

BRIEF DESCRIPTION OF THE DRAWINGS

FIG. 1 shows an isometric view of a dilution tunnel according to the invention;

FIG. 2 shows a side view in section of the dilution tunnel of FIG. 1;

FIG. 3 shows a block diagram of an emissions analysis system according to one embodiment the invention; and FIG. 4 shows a detail view of the system according to another embodiment of the invention.

DESCRIPTION OF THE PREFERRED EMBODIMENT

Referring to FIG. 1, a dilution tunnel 10 comprises an elongated, hollow tube 12 having an inlet 13 defined by an opening at an end of the tube 12. Preferably, the tube is a cylinder about 20 cm long, 5 cm in diameter, and made of aluminum, polyvinylchloride, or other suitable rigid and relatively inert material. These materials are preferred for their availability, light weight, low cost, and because they will not interact with or pass emissions through their surfaces. The tube may have a flexible portion 14, such as a corrugated wall.

Referring to FIG. 2, a screen 16, wire mesh, steel wool, or other diffusing device is disposed inside the tube 12 and spans the interior circumference of the tube. The screen 16 and interior walls of the tube 12 define a mixing zone 18 on the opposite side of the screen from the inlet 13, that is, the downstream side of the inlet.

A probe 20, such as a hollow tube is disposed through a wall of the tube 12 downstream of the inlet 13. The probe is preferably curved 90° so as to pass through the wall orthogonally to the surface of the tube and open toward the inlet 13 of the tube. Part of the probe which extends outside the tube 12 is equipped with a handle 21.

Referring to FIG. 3, the probe 20 is connected to a sample line 22, such as a pipe or tube, adapted to convey gas to a gas analyzer 24. The gas analyzer 24 comprises apparatus for analyzing a plurality of components of a gas including a carbon monoxide analyzer 26, a carbon dioxide analyzer 28, an oxygen analyzer 30, an oxides of nitrogen analyzer 32, and a hydrocarbon analyzer 34. In one embodiment shown in FIG. 4, sensors 35 of the analyzers are disposed in the tunnel 10, thereby eliminating the need for the probe and sample line. Returning to FIG. 3, a means for treating the emissions and air, such as a condenser 36, is disposed between the sample line 22 and certain analyzers, as necessary. A filter 37 for removing heavy particulate matter is disposed upstream of the carbon monoxide and carbon dioxide analyzers. A water trap, a pump or other treating means may be disposed in the sample line 22 upstream of all or some of the analyzers as desired or required. A computer 38 is preferably used to control the analyzer 24 and/or compile analysis data which can be output to a printer 39.

An engine 40 has an exhaust system including a muffler 42 and a tailpipe 44, the tailpipe being a source of emissions generated by the engine which is to be tested. These emissions are analyzed by the gas analyzer 24 to determine quantities of various components. The engine also includes a fuel line 46 for carrying fuel and a drive shaft 48 for transferring mechanical power.

For certain tests, such as air/fuel ratio analysis, it is preferable to use a fuel flow meter 50 connected to the fuel line 46 and the computer 38 to transmit fuel flow data to the computer. A dynamometer 52 is connected to the drive shaft 48 and the computer 38 to transmit engine speed and torque information to the computer. The fuel flow meter 50 and dynamometer 52 are not necessary to test emissions according to the invention, but are useful in measuring engine performance and other characteristics.

The dilution tunnel 10 is also provided with a means for spacing the inlet 13 from the tailpipe 44. The spacing means can be a spacer bracket 54, a ruler, a support for the tunnel, or the handle 21 held by a person, for example. The spacer is used to maintain the inlet 13 of the tunnel at a relatively constant distance from the tailpipe 44. The bracket 54 has a notch 56 which is braced against an edge of the tailpipe to maintain constant spacing between the inlet and the tailpipe. Alternatively, the spacer bracket could rest on the muffler or another part of the engine. For example, possible configuration comprises perforations 58 or other apertures in the tube upstream of the mixing screen 16, as shown in FIG. 4. It would be possible with such a configuration to use the end of the tube as the spacing means braced against the muffler 42 with the tailpipe 44 inside the tube so that dilution air enters through the perforations and the inlet 13 is effectively disposed upstream from the end of the tube near the screen 16. A wire extending across the inside of the tunnel near the inlet can be braced against the end of the tailpipe which is partly inside the tube 12. The inlet and the spacing means are such that no fixed connections to the sources of the emissions and dilution air are required and no separate or "artificial" means of urging or controlling flow of dilution air into the tunnel with the emissions is required. That is, the natural flow of emissions and air into the inlet provides sufficient dilution.

In operation, the engine 40 is running and emissions are directed from the engine, through the muffler and tailpipe, into the surrounding atmosphere. The dilution tunnel 10 is positioned so that its inlet 13 is spaced from the tailpipe 44 and emissions are directed through the inlet into the tube 12. The preferred distance is 1 to 2 cm, however, this is not critical. It is more important that the distance remain constant during analysis. Surrounding atmospheric air is entrained by the emissions flow and flows into the tube through the inlet 13 with the emissions. The air and emissions flow through the screen 16 where they are diffused and mixed in the mixing zone 18. Complete mixing of the gasses so that the components of the emissions are evenly distributed is important for accurate analysis of the emissions. A portion of the mixture flows into the probe 20 and is diverted, through the sample line 22, to the gas analyzer 24. The treatment means may condense, filter or otherwise treat the mixture prior to analyzing the various components of the emissions.

If, in addition to emissions data, information with respect to engine performance is desired, the dynamometer 52 and fuel flow meter 50 are connected as described above. The computer 38 compiles and analyzes data from the gas analyzer, dynamometer, and fuel flow meter to produce statistics regarding emissions content, engine performance, and relationships between these data.

The present disclosure describes several embodiments of the invention, however, the invention is not limited to these embodiments. Other variations are contemplated to be within the spirit and scope of the invention and appended claims.

What is claimed is:

1. A device for testing gaseous emissions from a gas exit, comprising:
    a dilution tunnel comprising an elongated, hollow tube having an inlet and an outlet;
    means for spacing said inlet of the tube inline from the gas exit so as to admit emissions and surrounding air into the dilution tunnel through the inlet; and
    means for analyzing the emissions in the tunnel.

2. A device according to claim 1, further comprising a sensor disposed in the tunnel and connected to the analyzing means.

3. A device according to claim 1, further comprising probe means disposed in the tunnel for diverting a portion of the emissions from the tunnel to the analyzing means.

4. A device according to claim 3, wherein the probe comprises a hollow tube.

5. A device according to claim 4, wherein the probe is disposed through a wall of the tunnel and opens toward the inlet.

6. A device according to claim 4, further comprising a means for treating the emissions and air disposed between the probe and at least part of the analyzing means.

7. A device according to claim 6, wherein the treating means is a condenser.

8. A device according to claim 6, wherein the treating means is a filter.

9. A device according to claim 1, wherein the air and emissions are mixed in the tunnel prior to being analyzed.

10. A device according to claim 1, wherein the analyzing means is adapted to analyze components of the emissions.

11. A device according to claim 1, wherein the tunnel is flexible.

12. A device according to claim 1, further comprising a means for diffusing the emissions and air disposed in the tunnel downstream of the inlet.

13. A device according to claim 1, further comprising a means for facilitating mixing of the air and emissions disposed in the tunnel downstream of the inlet.

14. A device according to claim 13, wherein the mixing means comprises a screen.

15. A device according to claim 1, further comprising a computer connected to the analyzing means.

16. A device according to claim 15, further comprising, a dynamometer connected to the computer and a drive shaft of an emissions generating engine; and a fuel flow meter connected to the computer and a fuel line of the engine.

17. A device for testing gaseous emissions from a gas exit, comprising:
    a dilution tunnel comprising an elongated, hollow tube having an inlet for emission gasses and an outlet;
    means for spacing the inlet inline from the gas exit so as to admit emissions and surrounding air into the dilution tunnel through the inlet;
    means for analyzing the emissions;
    a tubular probe disposed in the tunnel and opening toward the inlet for diverting a portion of the emissions from the tunnel to the analyzing means; and
    means for facilitating mixing of the air and emissions disposed in the tunnel between the inlet and the probe.

18. A method of testing gaseous emissions from a gas exit, comprising the steps of:
    locating an inlet of a dilution tunnel comprising an elongated, hollow tube a selected distance from the gas exit so as to be spaced inline from the gas exit so as to admit emissions and surrounding air into the tunnel through the inlet; and
    analyzing the emissions in the tunnel.

19. A method according to claim 18, further comprising the step of diverting a portion of the emissions and air in the tunnel by a probe means disposed in the tunnel to a means for analyzing the emissions wherein the emissions diverted by the probe are the emissions analyzed.

20. A method according to claim 18, further comprising the step of mixing the air and emissions in the tunnel.

* * * * *

UNITED STATES PATENT AND TRADEMARK OFFICE
CERTIFICATE OF CORRECTION

PATENT NO.   : 5,410,907
DATED        : May 2, 1995
INVENTOR(S)  : Hans Strom et al.

It is certified that error appears in the above-indentified patent and that said Letters Patent is hereby corrected as shown below:

On the ttile page, item [73] Assignee, should read--
White Consolidated Industries, Inc., Shreveport, LA--
Consolidated Industries, Inc., Shreveport, LA--.

On the title page, the following information should be inserted with respect to the Attorney, Agent or Firm: --Pearne, Gordon, McCoy & Granger--.

Signed and Sealed this

Sixteenth Day of July, 1996

Attest:

BRUCE LEHMAN

Attesting Officer    Commissioner of Patents and Trademarks